US 6,710,070 B2

(12) United States Patent
Druzgala

(10) Patent No.: US 6,710,070 B2
(45) Date of Patent: Mar. 23, 2004

(54) COMPOUNDS FOR TREATMENT OF CARDIAC ARRHYTHMIA, SYNTHESIS, AND METHODS OF USE

(75) Inventor: Pascal Druzgala, Santa Rosa, CA (US)

(73) Assignee: ARYx Therapeutics, Santa Clara, CA (US)

( * ) Notice: Subject to any disclaimer, the term of this patent is extended or adjusted under 35 U.S.C. 154(b) by 0 days.

(21) Appl. No.: 10/319,073

(22) Filed: Dec. 10, 2002

(65) Prior Publication Data

US 2003/0158194 A1 Aug. 21, 2003

Related U.S. Application Data

(60) Provisional application No. 60/339,898, filed on Dec. 10, 2001.

(51) Int. Cl.[7] ............... A61K 31/343; A61K 31/381; A61K 31/404; C07D 209/12; C07D 307/80
(52) U.S. Cl. ............... 514/419; 514/443; 514/469; 548/492; 549/57; 549/468
(58) Field of Search .................. 514/419, 443, 514/469; 548/492; 549/57, 468

(56) References Cited

U.S. PATENT DOCUMENTS

| | | |
|---|---|---|
| 4,931,464 A | 6/1990 | Grover et al. |
| 4,962,095 A | 10/1990 | Grover et al. |
| 5,175,187 A | 12/1992 | Baligadoo |
| 5,364,880 A | 11/1994 | Druzgala |
| 5,440,054 A | 8/1995 | Druzgala |
| 5,849,788 A | 12/1998 | Druzgala |
| 6,130,240 A | 10/2000 | Druzgala |
| 6,316,487 B1 | 11/2001 | Druzgala et al. |
| 6,362,223 B1 | 3/2002 | Druzgala et al. |
| 6,372,783 B1 | 4/2002 | Druzgala et al. |

Primary Examiner—Taofiq A. Solola
(74) Attorney, Agent, or Firm—Saliwanchik, Lloyd & Saliwanchik

(57) ABSTRACT

The subject invention pertains to novel compounds (and salts thereof), and compositions comprising the compounds, for the treatment of cardiac arrhythmias. The subject invention further concerns methods of making the novel compounds. The novel compounds are rapidly metabolized analogs of amiodarone, having the distinct and advantageous characteristic of being metabolized to a less lipophilic compound. This results in an improved safety profile. The new compounds have particular utility for treating life-threatening ventricular tachyarrhythmias, especially in patients with congestive heart failure (CHF). The compounds also provide effective management for ventricular arrhythmias and supraventricular arrhythmias, including atrial fibrillation and re-entrant tachyarrhythmias involving accessory pathways.

16 Claims, No Drawings

COMPOUNDS FOR TREATMENT OF CARDIAC ARRHYTHMIA, SYNTHESIS, AND METHODS OF USE

CROSS-REFERENCE TO RELATED APPLICATION(S)

This application claims the benefit of provisional patent application Ser. No. 60/339,898, filed Dec. 10, 2001, which is hereby incorporated by reference in its entirety.

BACKGROUND OF INVENTION

Congestive heart failure (CHF) is a disease affecting approximately 2% of the population of the United States (Sami, M. H. [1991] J. Clin. Pharmacol. 31:1081). Despite advances in the diagnosis and treatment of CHF, the prognosis remains poor with a 5-year mortality rate higher than 50% from the time of diagnosis (McFate Smith, W. [1985] Am. J. Cardiol. 55:3A; McKee, P. A., W. P. Castelli, P. M. McNamara, W. B. Kannel [1971] N. Engl. J. Med. 285:1441). In patients with CHF, the rate of survival is lowest in those patients with severe depression of left ventricular function and patients who have frequent ventricular arrhythmias. Patients with ventricular arrhythmias and ischemic cardiomyopathy have an increased risk of sudden death. The presence of ventricular tachycardia in patients with severe CHF results in a three-fold increase in sudden death compared to those without tachycardia (Bigger, J. T., Jr. [1987] Circulation 75 (Supplement IV):28). Because of the high prevalence of sudden unexpected death in patients with CHF, there has been a growing interest in the prognostic significance of arrhythmias in these patients.

Several compounds have been used in the management of cardiac arrhythmias in patients with congestive heart failure. Unfortunately, anti-arrhythmic drug therapy has been disappointing. The efficacy of anti-arrhythmic drugs markedly decreases as left ventricular function declines, such that only a small fraction of patients with CHF are responsive to anti-arrhythmic therapy. No anti-arrhythmic drug has prevented sudden death in patients with CHF. There is even a question of increased mortality associated with certain anti-arrhythmic drugs (the CAST investigators [1989] N. Engl. J. Med. 321:406).

Scientists define tachycardia and ventricular fibrillation as being of multiple nature. It now seems clear, and is accepted in the art, that re-entry is the underlying mechanism to most sustained arrhythmias. Prolonging ventricular repolarization as a means of preventing ventricular arrhythmias has consequently received renewed attention. This points to Class-III agents as drugs of choice in the treatment of arrhythmias. A Class-III agent, as referred to herein, is an agent which is classified as such in the Vaughan-Williams classification of anti-arrhythmic drugs. A Class-III agent exerts its primary anti-arrhythmic activity by prolonging cardiac action potential duration (APD), and thereby the effective refractory period (ERP), with no effect on conduction. These electrophysiological changes, which are brought about by blockade of cardiac potassium channels, are well known in the art. Because the blockade of cardiac potassium channels is not associated with depression of the contractile function of the heart, Class-III agents are particularly attractive for use in patients with CHF. Unfortunately, the existing Class-III agents are limited in their utility by additional pharmacological activities, lack of good oral bioavailability, or a poor toxicity profile. The only two Class III agents currently marketed are bretylium (i.v. only) and amiodarone (i.v. and p.o.).

Amiodarone is an anti-arrhythmic agent having vasodilator properties that may benefit patients with severe heart failure. Amiodarone has been shown to improve survival of post-myocardial infarction patients with asymptomatic high-grade entricular arrhythmias, and it proved efficacious in patients resistant to other anti-arrhythmic drugs without impairing left ventricular function. Cardioprotective agents and methods which employ amiodarone in synergistic combination with vasodilators and beta blockers have been described for use in patients with coronary insufficiency (U.S. Pat. No. 5,175,187). Amiodarone has also been described for reducing arrhythmias associated with CHF as used in combination with antihypertensive agents, e.g., (S)-1-[6-amino-2-[[hydroxy(4-phenylbutyl)phosphinyl] oxyl]-L-proline (U.S. Pat. No. 4,962,095) and zofenopril (U.S. Pat. No. 4,931,464). However, amiodarone is a difficult drug to manage because of its numerous side effects, some of which are serious.

The most serious long-term toxicity of amiodarone derives from its kinetics of distribution and elimination. It is absorbed slowly, with a low bioavailability and relatively long half-life. These characteristics have clinically important consequences, including the necessity of giving loading doses, a delay in the achievement of full anti-arrhythmic effects, and a protracted period of elimination of the drug after its administration has been discontinued.

Amiodarone also can interact negatively with numerous drugs including aprindine, digoxin, flecainide, phenytoin, procainamide, quinidine, and warfarin. It also has pharmacodynamic interactions with catecholamines, diltiazem, propranolol, and quinidine, resulting in alpha- and beta-antagonism, sinus arrest and hypotension, bradycardia and sinus arrest, and torsades de pointes and ventricular tachycardias, respectively. There is also evidence that amiodarone depresses vitamin K-dependent clotting factors, thereby enhancing the anticoagulant effect of warfarin.

Numerous adverse effects limit the clinical applicability of amiodarone. Important side effects can occur including corneal microdeposits, hyperthyroidism, hypothyroidism, hepatic dysfunction, pulmonary alveolitis, photosensitivity, dermatitis, bluish discoloration, and peripheral neuropathy.

There is no Class-III agent presently marketed that can be used safely in patients with CHF. The cardiovascular drug market is the largest in any field of drug research, and an effective and safe Class-III anti-arrhythmic agent useful in patients with CHF is expected to be of substantial benefit. Therefore, a drug which could successfully improve the prognosis of CHF patients, but with a safety profile much improved over that of amiodarone, would be extremely useful and desired. Various analogs of amiodarone have been previously described (U.S. Pat. Nos. 6,372,783; 6,362,223; 6,316,487; 6,130,240; 5,849,788; 5,440,054; and 5,364,880). The subject invention adds to this arsenal of compounds.

BRIEF SUMMARY

The subject invention provides novel compounds (and salts thereof), and compositions comprising the compounds, for the treatment of cardiac arrhythmias. The subject invention further concerns methods for making the novel compounds. The novel compounds are rapidly metabolized analogs of amiodarone, having the distinct and advantageous characteristic of being metabolized to a less lipophilic compound. This results in an improved safety profile.

The compounds of the subject invention have particular utility for treating life-threatening ventricular tachyarrhythmias, especially in patients with congestive heart failure (CHF). The compounds of the subject invention also provide effective management for ventricular arrhythmias and supraventricular arrhythmias, including atrial fibrillation and re-entrant tachyarrhythmias involving accessory pathways.

More specifically, the novel compounds have the particular advantage of reducing the numerous side effects observed with the drugs currently available for treatment of these cardiac arrhythmias. For example, the compound of choice currently used for treating cardiac arrhythmias is amiodarone, which has side effects that can be serious.

The subject invention thus involves the innovative development of a Class-III anti-arrhythmic agent having significantly lower toxicity than any currently available compound useful in patients with congestive heart failure (CHF).

DETAILED DISCLOSURE OF THE INVENTION

The subject invention concerns novel compounds which can produce the desired pharmacological properties of amiodarone but, unlike amiodarone, are susceptible to biotransformation by plasma and tissue esterases to give a carboxylic acid metabolite. Carboxylic acids form water-soluble salts at physiological pH, and therefore undergo renal elimination. Accordingly, long-term toxicity symptoms (pulmonary fibrosis, corneal microdeposits, etc.) decrease.

Preferred compounds of the invention have the following chemical structures:

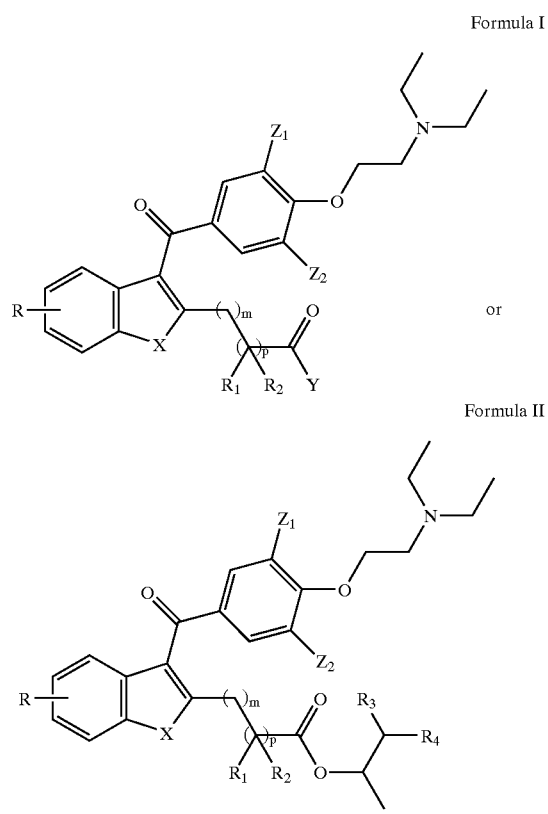

Formula I

Formula II wherein $Z_1$ and $Z_2$ may be the same, or different, and are a halogen selected from the group consisting of iodine, fluorine, bromine, and chlorine; X can be O, S, or NH;

m is from 0 to 4;

p is 0 or 1;

R=H, OH, $NH_2$, SH, halide, alkyl, O-alkyl, acyl, O-acyl, aryl, O-aryl, substituted amine, or substituted thiol;

$R_1$ and $R_2$ can be the same or different and are, independently H, methyl, ethyl, propyl, with the proviso that $R_1$ and $R_2$ are not both H. Alternatively, $R_1$ and $R_2$, together, can form a cyclopropyl, cyclobutyl, cyclopentyl, or a cyclohexyl group.

$Y=OR_5$, wherein $R_5$ is a straight or branched chain alkyl or heteroalkyl having 1 to 8 carbon atoms, a substituted or unsubstituted aryl or heteroaryl; or

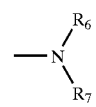

wherein $R_6$ and $R_7$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and $R_3$ and $R_4$ can be the same or different and can be a moiety selected from the group consisting of $C_{n-20}$alkyl, $C_{n-20}$ heteroalkyl, $C_{2-20}$ alkenyl, aryl, $C_{1-20}$ alkyl-aryl, $C_{2-20}$ alkenyl-aryl, heteroaryl, $C_{1-20}$alkyl-heteroaryl, $C_{2-20}$ alkenyl-heteroaryl, cycloalkyl, heterocycloalkyl, $C_{1-20}$ alkyl-heterocycloalkyl, and $C_{1-20}$ alkyl-cycloalkyl, any of which may be, optionally, substituted with a moiety selected from the group consisting of $C_{1-6}$ alkyl, halogen, CN, $NO_2$, or $SO_{2-4}$, or wherein N is part of a cyclic or heterocyclic group, preferentially, but not limited to, morpholine, triazole, imidazole, pyrrolidine, piperidine, piperazine, pyrrole, dihydropyridine, aziridine, thiazolidine, thiazoline, thiadiazolidine, or thiadiazoline; wherein n is from 1–19.

Because n can be from 1 to 19, the term "$C_{n-20}$ alkyl" refers to straight or branched chain alkyl moiety having from one to twenty carbon atoms, including for example, methyl, ethyl, propyl, isopropyl, butyl, tert-butyl, pentyl, hexyl and the like. In one embodiment, n is at least one, in an alternative embodiment, n is at least 2.

The term "$C_{2-20}$ alkenyl" refers to a straight or branched chain alkyl moiety having two to twenty carbon atoms and having at least one double bond. This term would include for example, vinyl, 1-propenyl, 1- and 2-butenyl, 2-methyl-2-propenyl etc.

The term "cycloalkyl" refers to a saturated alicyclic moiety having from three to six carbon atoms and which is optionally benzofused at any available position. This term includes for example cyclopropyl, cyclobutyl, cyclopentyl, cyclohexyl, indanyl and tetrahydronaphthyl.

The term "heterocycloalkyl" refers to a saturated heterocyclic moiety having from three to six atoms. One or more of these atoms may be heteroatoms selected from N, O, S and oxidized versions thereof, and which is optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having from three to six carbon atoms and having at least one double bond. This term includes, for example, cyclopentenyl and cyclohexenyl.

The term "heterocycloalkenyl" refers to an alicyclic moiety having from three to six atoms. One, or more, of these atoms may be heteroatoms selected from N, O, S and oxidized versions thereof, and having in addition one double bond. This term includes, for example, dihydropyranyl.

The term "aryl" refers to an aromatic carbocyclic radical having a single ring or two condensed rings. This term includes, for example phenyl or naphthyl.

The term "heteroaryl" refers to aromatic ring systems of five to ten atoms of which at least one atom is selected from O, N and S, and includes, for example, furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

In certain preferred embodiments, $Z_1$ and $Z_2$ are iodine, m=0 or 1, at least one of $R_1$ or $R_2$ is methyl and the other is H or methyl, and where $R_5$ is H, methyl, ethyl, propyl, isopropyl, butyl, isobutyl, (R,S)-2-butyl, (S)-2-butyl, or (R)-2-butyl.

The novel compounds can also be provided in their salt form. Thus, the invention includes pharmaceutically acceptable salts, for example acid addition salts derived from inorganic or organic acids, such as hydrochlorides, hydrobromides, p-toluenesulfonates, phosphates, sulfates, perchlorates, acetates, trifluororacetates, proprionates, citrates, malonates, succinates, lactates, oxalates, tartrates, and benzoates. Salts may also be derived from bases (organic and inorganic), such as alkali metal salts (e.g., magnesium or calcium salts), or organic amine salts, such as morpholine, piperidine, dimethylamine, or diethylamine salts.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

The subject invention further pertains to enantiomerically isolated compounds, and compositions comprising the compounds, for calcium channel blocking. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

A further aspect of the subject invention pertains to the breakdown products which are produced when the therapeutic compounds of the subject invention are acted upon by hydrolytic enzymes, such as esterases. The presence of these breakdown products in urine or serum can be used to monitor the rate of clearance of the therapeutic compound from a patient.

The successful application of the new compounds to the treatment of CHF is evidenced by the evaluation of the thermodynamic properties of the compound, e.g., measuring its partition coefficient between water and octanol, evaluation of its kinetics of elimination by measuring its stability in buffer and in human plasma, and evaluation of its electrophysiological properties in guinea pig heart preparations.

More specifically, the novel compounds can be used for treating life-threatening ventricular tachyarrhythmias, especially in patients with congestive heart failure. This product can provide effective management of not only ventricular tachyarrhythmias and less severe ventricular arrhythmias, but also atrial fibrillation and re-entrant tachyarrhythmias involving accessory pathways. A composition comprising a novel compound having a rapid elimination rate can offer many advantages over the currently available anti-arrhythmic agents such as amiodarone.

These advantages include:

(i) a shorter onset of action, (ii) decreased and more manageable long-term toxicity, and (iii) lower potential for drug interactions.

In addition, the novel compounds can be included in a composition comprising a second active ingredient. The second active ingredient can be useful for concurrent or synergistic treatment of arrhythmia or for the treatment of an unrelated condition which can be present with or result from arrhythmia or CHF.

The subject compounds have thermodynamic properties similar to those of amiodarone, but provide the advantageous property of being rapidly metabolized in plasma to a water-soluble metabolite. More specifically, the subject compounds are Class-III agents with electronic, steric, and thermodynamic properties comparable to those of amiodarone, but with an enzymatically labile ester group advantageously built into the structure such that the drug can be readily hydrolyzed in plasma to a polar, water-soluble metabolite. This water-soluble metabolite can be eliminated by the kidneys. This is a definite advantage over amiodarone, which is metabolized primarily in the liver. Under such conditions, the elimination of the novel compounds are increased and results in a more rapid dissociation of the drug from phospholipid-binding sites. The accumulation of the compound, which is dependent on the steady-state tissue concentration of the drug, and therefore on the dose, then becomes easily reversible. It follows that, upon discontinuation of a drug comprising one of the novel compounds, clearance from the body is more rapid. This increased elimination makes anti-arrhythmic therapy using the subject compounds or compositions comprising the subject compounds easier to manage.

Furthermore, the compounds of the invention may be administered in conjunction with other compounds, or compositions thereof. These compounds, and compositions thereof, may include additional compounds known to be useful for the treatment of cardiac arrhythmias, cardioprotective agents, antibiotics, antiviral agents, or thrombolytic agents (e.g., streptokinase, tissue plasminogen activator, or recombinant tissue plasminogen activator). The compounds and compositions of the invention can have particular usefulness for treating life-threatening ventricular tachyarrhythmias, especially in patients with congestive heart failure (CHF). Post-myocardial infarction patients can also benefit from the administration of the subject compounds and compositions; thus, methods of treating post-myocardial infarction patients are also provided by the subject invention. An "individual" or "patent" includes animals and humans in need of treatment for arrhythmias. In a preferred embodiment, the individual is a human.

Cardioprotective agents include vasodilators and beta blockers described for use in patients with coronary insufficiency (such as those of U.S. Pat. No. 5,175,187 or others known to the skilled artisan). Other cardioprotective agents include known anti-hypertensive agents, e.g., (S)-1-[6-amino-2-[[hydroxy(4-phenylbutyl)phosphinyl]oxyl]-L-proline (U.S. Pat. No. 4,962,095) and zofenopril (U.S. Pat. No. 4,931,464). Additional cardioprotective agents include, but are not limited to, aspirin, heparin, warfarin, digitalis, digitoxin, nitroglycerin, isosorbide dinitrate, hydralazine, nitroprusside, captopril, enalapril, and lisinopril.

The compounds and compositions also provide effective management for ventricular arrhythmias and supraventricular arrhythmias, including atrial fibrillation and re-entrant tachyarrhythmias involving accessory pathways. Compounds and compositions of the invention are also useful for the treatment of ventricular and supra-ventricular arrhythmias, including atrial fibrillation and flutter, paroxysmal supraventricular tachycardia, ventricular premature beats (VPB), sustained and non-sustained ventricular tachycardia (VT), and ventricular fibrillation (VF). Other non-limiting examples of the arrhythmias which may be treated by the compounds of the instant invention include: narrow QRS tachycardia (atrial, intra-/para-A-V node, or accessory pathway),ventricular tachycardia, and ventricular arrhythmias in cardiomyopathy.

The compounds of this invention have therapeutic properties similar to those of the unmodified parent compounds. Accordingly, dosage rates and routes of administration of the disclosed compounds are similar to those already used in the art and known to the skilled artisan. (See, for example, *Physicians' Desk Reference*. 54$^{th}$ Ed., Medical Economics Company, Montvale, N.J., 2000.)

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulation which can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenges.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. A more complete understanding of the invention can be obtained by reference to the following specific examples of compounds of the invention. It will be apparent to those skilled in the art that the examples involve use of materials and reagents that are commercially available from known sources, e.g., chemical supply houses, so no details are given respecting them. These examples should not be construed as limiting. All percentages are by weight and all solvent mixture proportions are by volume unless otherwise noted.

EXAMPLE 1

Synthesis Scheme for an Exemplary Novel Compound

Compound 1 (7.0 g) (U.S. Pat. No. 5,440,054, P. Druzgala, hereby incorporated by reference in its entirety) is dissolved in methanol (50 ml) at 0° C. containing 0.54 g of sodium methoxide. Methyl iodide (1.42 g) is added and the mixture is stirred at room temperature for 4 hours. The solvent is evaporated and the residue is dissolved in methylene chloride and washed with 2 portions of water (50 ml each portion). The product, compound 2, is purified on silica column with 5% methanol in methylene chloride as eluent.

Compound 2 (7.2 g) is dissolved in methanol (50 ml) at 0° C. containing 0.54 g of sodium methoxide. Methyl iodide (1.42 g) is added and the mixture is stirred at room temperature for 8 hours. The solvent is evaporated and the residue is dissolved in methylene chloride and washed with 2 portions of water (50 ml each portion). The product, compound 3, is purified on silica column with 5% methanol in methylene chloride as eluent.

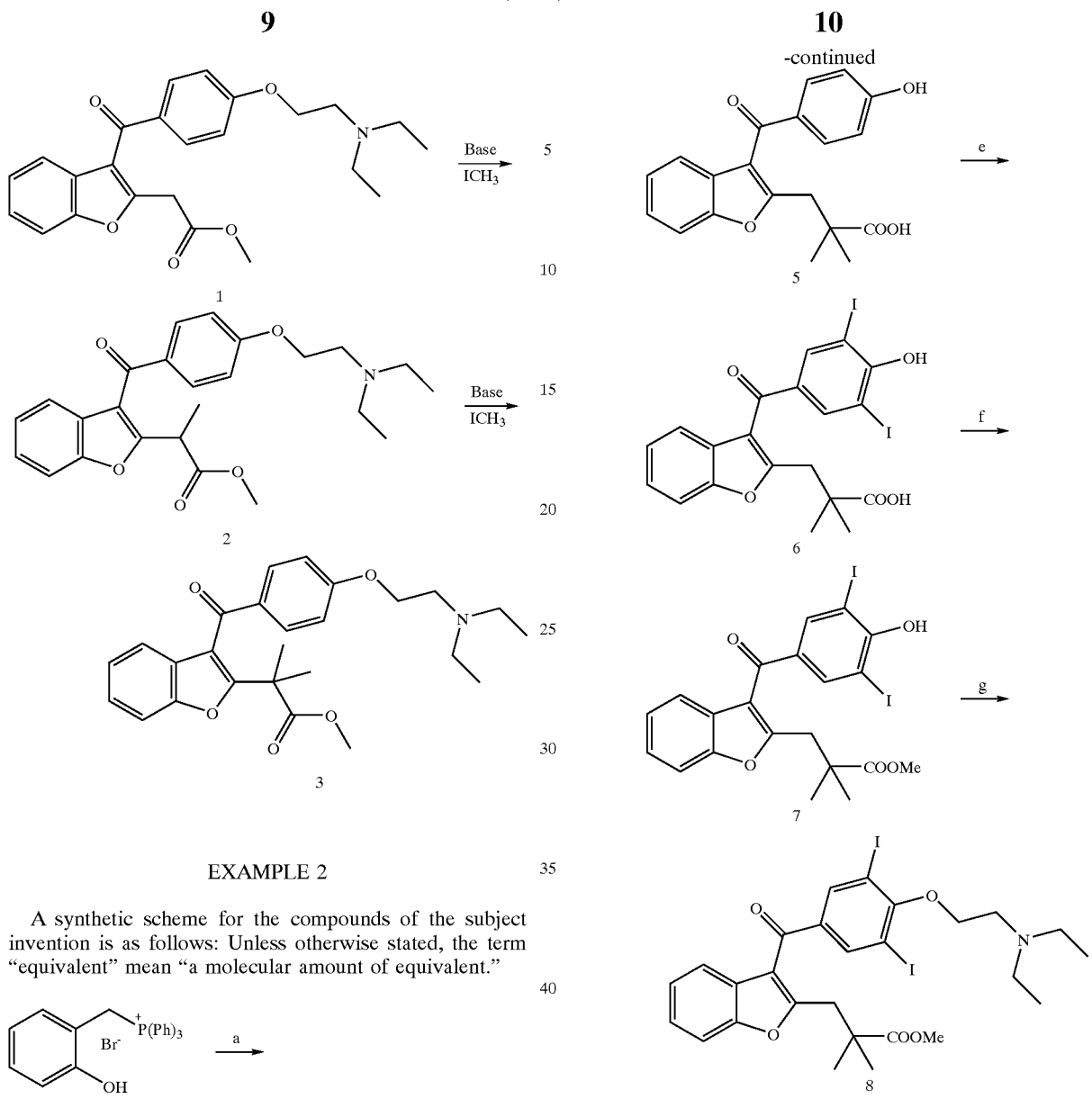

EXAMPLE 2

A synthetic scheme for the compounds of the subject invention is as follows: Unless otherwise stated, the term "equivalent" mean "a molecular amount of equivalent."

Compound 1 (1 equivalent), and methyl succinyl chloride (1.5 equivalents) in methylene chloride, are stirred with pyridine (2 equivalents) at reflux for 3 hours. The solvent is evaporated and anhydrous toluene is added. Add triethylamine (3 equivalents) and stir at reflux for 8 hours. Evaporate solvent and purify on silica, eluting with 5% ethyl acetate in hexane. The yield is about 80% of compound 2 as a white solid.

Compound 2 is then treated with 2 equivalents of sodium hydride in anhydrous DMF, at 0C. under argon. Then 2 equivalents of methyl iodide are added. After stirring at room temperature for 2 hours, the reaction is worked up as usual to give compound 3.

Compound 3 is dissolved in anhydrous methylene chloride and p-anisoyl chloride (1 equivalent) is added. Then add tin(IV) chloride and stir overnight at room temperature. Pour in ice-water and extract with methylene chloride. Dry over sodium sulfate and evaporate solvent. The product, compound 4, is a tan-colored solid.

Compound 4 is dissolved in methylene chloride. To the solution is added 5 equivalents of aluminum chloride and 10 equivalents of propanethiol. Stir for 12 hours at room temperature and then pour into ice-water. Keep the organic phase. Dry over sodium sulfate and evaporate the solvent. The product is a tan-colored solid, compound 5.

Compound 5 is dissolved in water containing 3 equivalents of sodium carbonate. Add 2 equivalents of iodine pellets (or flakes) and then stir at room temperature for 4 hours. Acidify with dilute HCl and filter the resulting solid that appears. Wash the solid with water. Dry in vacuo at 50C. The product, compound 6, is a solid.

Compound 6 is dissolved in 10 equivalents of methanol containing between 5 and 10% of its weight in sulfuric acid. Stir at reflux for 5 hours. Cool down to between 4 and 8C. The product, compound 7, crystallizes out of solution and is filtered off and dried.

Compound 7 is dissolved into a 50:50 mixture of methylene chloride and water. Add 2.3 equivalents of sodium hydroxide, 1.3 equivalents of diethylaminoethyl chloride, hydrochloride salt, and 0.1 equivalent of benzyltriethylammonium chloride. Stir vigorously at room temperature for 2 hours. Keep the organic phase. Evaporate solvent and purify on silica, eluting with 5% methanol in methylene chloride. The product, compound 8, is an oil.

Salts of compound 8 can be made. The salts are usually crystalline solids that can be crystallized from solvents such as acetone or even water. For example, 1 mmole of compound 8 is mixed with 1 mmole of citric acid in 10 ml of hot acetone. The citrate salt crystallizes upon cooling and is filtered off and dried. Other salts can be made in similar manner, chosing the solvent so that the salt crystallizes out upon cooling. Acceptable salts are, among others, tartrate, sulfate, phosphate, hydrochloride, succinate, fumarate, maleate, methanesulfonate.

It should be understood that the examples and embodiments described herein are for illustrative purposes only and that various modifications or changes in light thereof will be suggested to persons skilled in the art and are to be included within the spirit and purview of this application.

I claim:

1. A compound, or a salt thereof, wherein said compound has the following structures:

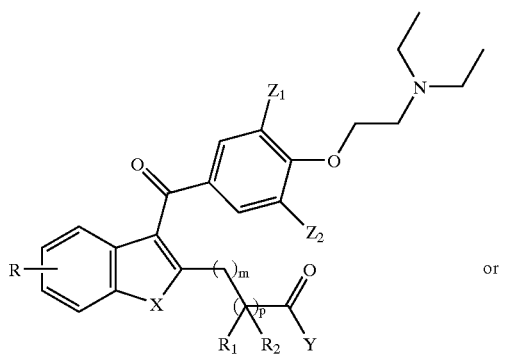

Formula I or

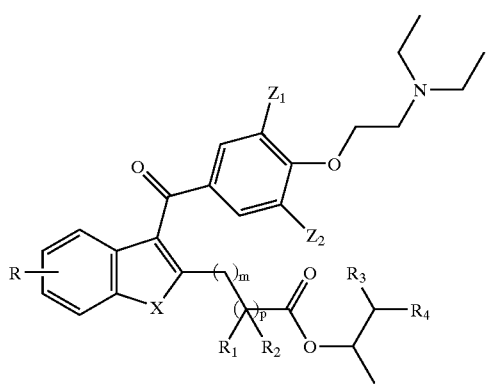

Formula II wherein $Z_1$ and $Z_2$ may be the same, or different, and are a halogen selected from the group consisting of iodine, fluorine, bromine, and chlorine; X can be O, S, or NH; m is from 0 to 4;
p is 0 or 1;
R=H, OH, $NH_2$, SH, halide, alkyl, O-alkyl, acyl, O-acyl, aryl, O-aryl, substituted amine, or substituted thiol;
$R_1$ and $R_2$ can be the same or different and are, independently H, methyl, ethyl, propyl, with the proviso that $R_1$ and $R_2$ are not both H; alternatively, $R_1$ and $R_2$, together, can form a cyclopropyl, cyclobutyl, cyclopentyl, or a cyclohexyl group;
Y=$OR_5$, wherein $R_5$ is a straight or branched chain alkyl or heteroalkyl having 1 to 8 carbon atoms, a substituted or unsubstituted aryl or heteroaryl; or

wherein $R_6$ and $R_7$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and
$R_3$ and $R_4$ can be the same or different and can be a moiety selected from the group consisting of $C_{n-20}$alkyl, $C_{n-20}$ heteroalkyl, $C_{2-20}$ alkenyl, aryl, $C_{1-20}$ alkyl-aryl, $C_{2-20}$ alkenyl-aryl, heteroaryl, $C_{1-20}$alkyl-heteroaryl, $C_{2-20}$ alkenyl-heteroaryl, cycloalkyl, heterocycloalkyl, $C_{1-20}$ alkyl-heterocycloalkyl, and $C_{1-20}$ alkyl-cycloalkyl, any of which may be, optionally, substituted with a moiety selected from the group consisting of $C_{1-6}$ alkyl, halogen, CN, $NO_2$, or $SO_{2-4}$, or wherein N is part of a cyclic or heterocyclic group.

2. The compound, according to claim 1, wherein R is H and X is O.

3. The compound, according to claim 1, wherein the salt of said compound is selected from the group consisting of hydrobromide, hydrochloride, malate, p-toluenesulfonate, phosphate, sulfate, perchlorate, acetate, trifluororacetate, proprionate, citrate, malonate, succinate, lactate, tartrate, benzoate, morpholine, piperidine, dimethylamine, and diethylamine salts.

4. The compound, according to claim 3, wherein the salt of said compound is a sulfate salt.

5. The compound, according to claim 1, wherein $X_1$ and $X_2$ are iodine, m=1, p=1, at least one of $R_1$ and $R_2$ is methyl and the other is H or methyl, and $R_5$ is selected from the group consisting of methyl, ethyl, propyl, isopropyl, butyl, isobutyl, (R,S)-2-butyl, (S)-2-butyl, and (R)-2-butyl.

6. The compound, according to claim 1, in substantially single enantiomer form having at least 80% enantiomeric excess.

7. A pharmaceutical composition for treating cardiac arrhythmia in an animal wherein said pharmaceutical composition comprises a compound, or salt thereof, wherein said compound has one of the following structures:

Formula I

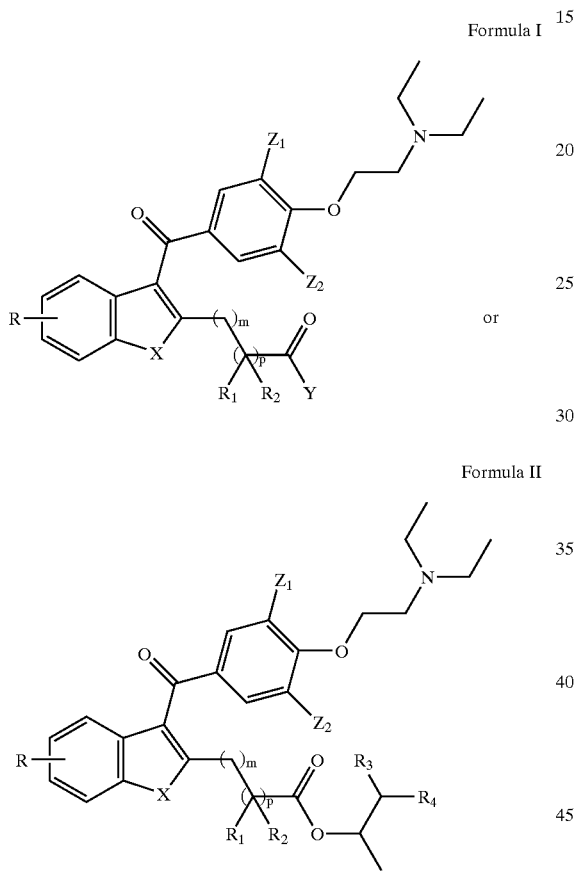

Formula II wherein $Z_1$ and $Z_2$ may be the same, or different, and are a halogen selected from the group consisting of iodine, fluorine, bromine, and chlorine; X can be O, S, or NH;

m is from 0 to 4;

p is 0 or 1;

R=H, OH, $NH_2$, SH, halide, alkyl, O-alkyl, acyl, O-acyl, aryl, O-aryl, substituted amine, or substituted thiol;

$R_1$ and $R_2$ can be the same or different and are, independently H, methyl, ethyl, propyl, with the proviso that $R_1$ and $R_2$ are not both H; alternatively, $R_1$ and $R_2$, together, can form a cyclopropyl, cyclobutyl, cyclopentyl, or a cyclohexyl group;

Y=$OR_5$, wherein $R_5$ is a straight or branched chain alkyl or heteroalkyl having 1 to 8 carbon atoms, a substituted or unsubstituted aryl or heteroaryl; or

wherein $R_6$ and $R_7$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and $R_3$ and $R_4$ can be the same or different and can be a moiety selected from the group consisting of $C_{n-20}$alkyl, $C_{n-20}$ heteroalkyl, $C_{2-20}$ alkenyl, aryl, $C_{1-20}$ alkyl-aryl, $C_{2-20}$ alkenyl-aryl, heteroaryl, $C_{1-20}$alkyl-heteroaryl, $C_{2-20}$ alkenyl-heteroaryl, cycloalkyl, heterocycloalkyl, $C_{1-20}$ alkyl-heterocycloalkyl, and $C_{1-20}$ alkyl-cycloalkyl, any of which may be, optionally, substituted with a moiety selected from the group consisting of $C_{1-6}$ alkyl, halogen, CN, $NO_2$, or $SO_{2-4}$, or wherein N is part of a cyclic or heterocyclic group.

8. The pharmaceutical composition, according to claim 7, wherein R is H and X is O.

9. The pharmaceutical composition, according to claim 7, wherein the salt of said compound is selected from the group consisting of hydrobromide, p-toluenesulfonate, hydrochloride, malate, phosphate, sulfate, perchlorate, acetate, trifluororacetate, proprionate, citrate, malonate, succinate, lactate, tartrate, benzoate, morpholine, piperidine, dimethylamine, and diethylamine salts.

10. The pharmaceutical composition, according to claim 9, wherein the salt of said compound is a sulfate salt.

11. The pharmaceutical composition, according to claim 6, wherein wherein $X_1$ and $X_2$ are iodine, m=1, p=1, at least one of $R_1$ and $R_2$ is methyl and the other is H or methyl, and $R_5$ is selected from the group consisting of methyl, ethyl, propyl, isopropyl, butyl, isobutyl, (R,S)-2-butyl, (S)-2-butyl, and (R)-2-butyl.

12. A method for treating cardiac arrhythmia in an animal, wherein said method comprises administering an effective amount of a compound, or salt thereof, wherein said compound has one of the following structures:

Formula I

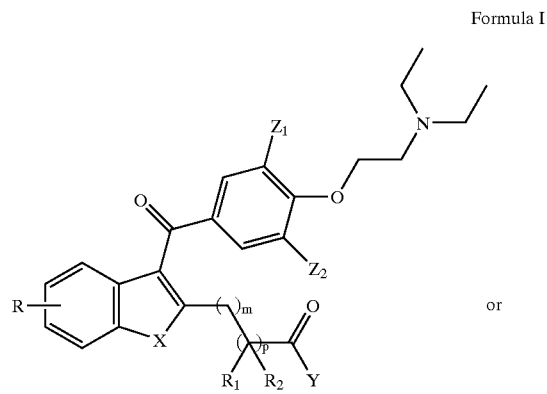

Formula II

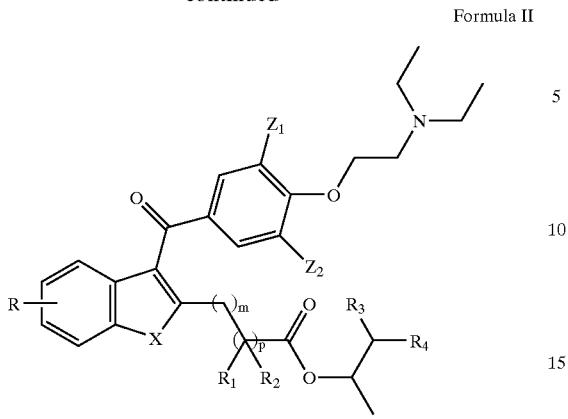

wherein $Z_1$ and $Z_2$ may be the same, or different, and are a halogen selected from the group consisting of iodine, fluorine, bromine, and chlorine; X can be O, S, or NH;

m is from 0 to 4;

p is 0 or 1;

R=H, OH, $NH_2$, SH, halide, alkyl, O-alkyl, acyl, O-acyl, aryl, O-aryl, substituted amine, or substituted thiol;

$R_1$ and $R_2$ can be the same or different and are, independently H, methyl, ethyl, propyl, with the proviso that $R_1$ and $R_2$ are not both H; alternatively, $R_1$ and $R_2$, together, can form a cyclopropyl, cyclobutyl, cyclopentyl, or a cyclohexyl group;

Y=$OR_5$, wherein $R_5$ is a straight or branched chain alkyl or heteroalkyl having 1 to 8 carbon atoms, a substituted or unsubstituted aryl or heteroaryl; or

wherein $R_6$ and $R_7$ are independently selected from H, alkyl or heteroalkyl of 1 to 6 carbon atoms, or wherein N is part of a cyclic or heterocyclic group comprising morpholine, triazole, imidazole, pyrrolidine, piperidine, piperazine, pyrrole, dihydropyridine, aziridine, thiazolidine, thiazoline, thiadiazolidine, or thiadiazoline; and $R_3$ and $R_4$ can be the same or different and can be a moiety selected from the group consisting of $C_{n-20}$alkyl, $C_{n-20}$ heteroalkyl, $C_{2-20}$ alkenyl, aryl, $C_{1-20}$ alkyl-aryl, $C_{2-20}$ alkenyl-aryl, heteroaryl, $C_{1-20}$alkyl-heteroaryl, $C_{2-20}$ alkenyl-heteroaryl, cycloalkyl, heterocycloalkyl, $C_{1-20}$ alkyl-heterocycloalkyl, and $C_{1-20}$ alkyl-cycloalkyl, any of which may be, optionally, substituted with a moiety selected from the group consisting of $C_{1-6}$ alkyl, halogen, CN, $NO_2$, or $SO_{2-4}$, or wherein N is part of a cyclic or heterocyclic group.

13. The method, according to claim 12, wherein R is H and X is O.

14. The method, according to claim 12, wherein said composition is administered to a mammal.

15. The method, according to claim 14, wherein said composition is administered to a human.

16. The method, according to claim 12, wherein said composition is administered in combination with a second pharmaceutical composition.

* * * * *